(12) United States Patent
Pedersen et al.

(10) Patent No.: US 11,969,581 B2
(45) Date of Patent: Apr. 30, 2024

(54) AUTO INJECTOR WITH ADAPTABLE AIR-SHOT MECHANISM

(71) Applicant: Ascendis Pharma A/S, Hellerup (DK)

(72) Inventors: Per Mølgaard Pedersen, Struer (DK); Flemming Madsen, Aalborg SV (DK); Sven Erik Poulsen, Skive (DK); Steen Jensen, Dragør (DK); Henrik Egesborg, Hellerup (DK)

(73) Assignee: Ascendis Pharma A/S, Hellerup (DK)

( * ) Notice: Subject to any disclaimer, the term of this patent is extended or adjusted under 35 U.S.C. 154(b) by 0 days.

(21) Appl. No.: 17/816,360

(22) Filed: Jul. 29, 2022

(65) Prior Publication Data

US 2023/0016657 A1    Jan. 19, 2023

Related U.S. Application Data

(63) Continuation of application No. 16/060,606, filed as application No. PCT/EP2016/082859 on Dec. 29, 2016, now Pat. No. 11,517,673.

(30) Foreign Application Priority Data

Dec. 30, 2015  (EP) ..................................... 15203171

(51) Int. Cl.
*A61M 5/31* (2006.01)
*A61M 5/20* (2006.01)
(Continued)

(52) U.S. Cl.
CPC ............ *A61M 5/3146* (2013.01); *A61M 5/20* (2013.01); *A61M 5/24* (2013.01);
(Continued)

(58) Field of Classification Search
CPC ............ A61M 5/3146; A61M 5/31511; A61M 2205/215; A61M 2205/6018;
(Continued)

(56) References Cited

U.S. PATENT DOCUMENTS

| | | |
|---|---|---|
| 4,024,864 A | 5/1977 | Davies |
| 4,677,980 A | 7/1987 | Reilly et al. |
| | (Continued) | |

FOREIGN PATENT DOCUMENTS

| | | |
|---|---|---|
| CN | 101905048 | 12/2010 |
| CN | 102413855 | 4/2012 |
| | (Continued) | |

OTHER PUBLICATIONS

English Translation of Office Action dated Jun. 3, 2021, in Corresponding Chinese Application No. 201880043795.0.

(Continued)

*Primary Examiner* — Tasnim Mehjabin Ahmed
(74) *Attorney, Agent, or Firm* — Knobbe, Martens, Olson & Bear, LLP

(57) ABSTRACT

Disclosed is an auto injector for administering a medicament. The auto injector comprising: a housing; a cartridge receiver configured to receive a cartridge assembly comprising a cartridge and a cartridge code feature, the cartridge containing the medicament; a code sensor configured to read the cartridge code feature; a drive module coupled to move a plunger rod; and a processing unit coupled to the code sensor and the drive module. The processing unit being configured to: receive from the code sensor a code signal indicative of the cartridge code feature; control the drive module to move the plunger rod to a first plunger rod position, the first plunger rod position being based on the code signal; receive a trigger event; control the drive module to move the plunger rod to a second plunger rod position following reception of the trigger event.

15 Claims, 6 Drawing Sheets

(51) Int. Cl.
*A61M 5/24* (2006.01)
*A61M 5/315* (2006.01)

(52) U.S. Cl.
CPC . *A61M 5/31511* (2013.01); *A61M 2005/2411* (2013.01); *A61M 2205/215* (2013.01); *A61M 2205/3368* (2013.01); *A61M 2205/6018* (2013.01); *A61M 2205/6054* (2013.01); *A61M 2205/6063* (2013.01); *A61M 2205/6072* (2013.01)

(58) Field of Classification Search
CPC .. A61M 2205/6054; A61M 2205/6072; A61M 2205/6063
See application file for complete search history.

(56) References Cited

U.S. PATENT DOCUMENTS

| | | |
|---|---|---|
| 5,739,508 A | 4/1998 | Uber, III |
| 5,808,203 A | 9/1998 | Nolan, Jr. et al. |
| 6,368,314 B1 | 4/2002 | Kipfer et al. |
| 9,173,995 B1 | 11/2015 | Tucker |
| 10,384,031 B1 | 8/2019 | Acker et al. |
| 10,835,677 B2 | 11/2020 | Fabricius et al. |
| 11,179,524 B2 | 11/2021 | Pedersen et al. |
| 11,351,305 B2 | 6/2022 | Pedersen et al. |
| 11,406,760 B2 | 8/2022 | Olesen et al. |
| 11,517,673 B2 | 12/2022 | Pedersen et al. |
| 11,524,115 B2 | 12/2022 | Jacobsen et al. |
| 11,607,496 B2 | 3/2023 | Fabricius et al. |
| 11,684,724 B2 | 6/2023 | Egesborg et al. |
| 11,738,147 B2 | 8/2023 | Olesen et al. |
| 2002/0016573 A1 | 2/2002 | Munk |
| 2002/0107477 A1 | 8/2002 | Kipfer |
| 2003/0083626 A1* | 5/2003 | Munk ............... A61M 5/20 604/186 |
| 2003/0205587 A1 | 11/2003 | Tribe |
| 2005/0261634 A1 | 11/2005 | Karlsson |
| 2006/0178630 A1 | 8/2006 | Bostrom et al. |
| 2009/0036846 A1 | 2/2009 | Dacquay et al. |
| 2009/0209883 A1 | 8/2009 | Higgins et al. |
| 2009/0299328 A1 | 12/2009 | Mudd et al. |
| 2010/0069842 A1 | 3/2010 | Dos Santos et al. |
| 2010/0094309 A1 | 4/2010 | Boukhny et al. |
| 2010/0211005 A1 | 8/2010 | Edwards et al. |
| 2011/0313395 A1* | 12/2011 | Krulevitch ...... A61M 5/31525 604/82 |
| 2012/0078185 A1 | 3/2012 | Smith et al. |
| 2012/0204997 A1 | 8/2012 | Winn et al. |
| 2012/0283655 A1 | 11/2012 | Plumptre et al. |
| 2013/0079708 A1 | 3/2013 | Wiimpenny et al. |
| 2013/0193073 A1 | 8/2013 | Hogard et al. |
| 2013/0211326 A1 | 8/2013 | Dasbach et al. |
| 2013/0211327 A1 | 8/2013 | Osman et al. |
| 2013/0226134 A1 | 8/2013 | Schabbach et al. |
| 2013/0245545 A1 | 9/2013 | Arnold et al. |
| 2013/0281965 A1 | 10/2013 | Kamen et al. |
| 2013/0296807 A1 | 11/2013 | Lintern et al. |
| 2014/0012229 A1 | 1/2014 | Bokelman et al. |
| 2014/0114277 A1 | 4/2014 | Eggert et al. |
| 2014/0142514 A1 | 5/2014 | Elahi et al. |
| 2014/0166915 A1 | 6/2014 | Ishibashi et al. |
| 2014/0188076 A1 | 7/2014 | Kamen et al. |
| 2014/0193788 A1 | 7/2014 | Groves et al. |
| 2014/0207106 A1 | 7/2014 | Bechmann et al. |
| 2014/0221925 A1 | 8/2014 | Kondoh et al. |
| 2014/0358093 A1 | 12/2014 | Soerensen et al. |
| 2015/0045729 A1 | 2/2015 | Denzer et al. |
| 2015/0051538 A1 | 2/2015 | Hata et al. |
| 2015/0088089 A1 | 3/2015 | Bartlett, II et al. |
| 2015/0122338 A1* | 5/2015 | Hunter .............. A61M 5/3146 137/154 |
| 2015/0231334 A1 | 8/2015 | Buchine et al. |
| 2015/0306316 A1 | 10/2015 | Bruggemann |
| 2015/0320932 A1 | 11/2015 | Draper et al. |
| 2015/0359967 A1 | 12/2015 | Steel et al. |
| 2015/0367074 A1 | 12/2015 | Draper et al. |
| 2015/0367075 A1 | 12/2015 | Cave |
| 2015/0374930 A1 | 12/2015 | Hyde et al. |
| 2017/0119969 A1 | 5/2017 | McCullough et al. |
| 2017/0196702 A1 | 7/2017 | Agarwal |
| 2018/0094309 A1 | 4/2018 | Boukhany |
| 2018/0236181 A1 | 8/2018 | Marlin et al. |
| 2019/0009029 A1 | 1/2019 | Fabricius et al. |
| 2020/0384207 A1 | 12/2020 | Egesborg et al. |
| 2022/0152310 A1 | 5/2022 | Pedersen et al. |
| 2022/0288316 A1 | 9/2022 | Olesen et al. |
| 2023/0072178 A1 | 3/2023 | Jacobsen et al. |
| 2023/0090661 A1 | 3/2023 | Jensen et al. |
| 2023/0263961 A1 | 8/2023 | Egesborg et al. |
| 2023/0270945 A1* | 8/2023 | Fabricius .......... A61M 5/31511 604/89 |
| 2023/0338659 A1 | 10/2023 | Olesen et al. |

FOREIGN PATENT DOCUMENTS

| | | |
|---|---|---|
| CN | 102740907 | 10/2012 |
| CN | 103813820 | 5/2014 |
| CN | 105492047 | 4/2016 |
| EP | 2656865 | 10/2013 |
| EP | 2675500 | 12/2013 |
| EP | 2777731 | 9/2014 |
| EP | 2923715 | 9/2015 |
| GB | 2356349 | 5/2001 |
| GB | 2506918 | 4/2014 |
| JP | H11513586 | 11/1999 |
| JP | 2000-513973 | 10/2000 |
| JP | 2005-503202 | 2/2005 |
| JP | 2005-080832 | 3/2005 |
| JP | 2008-531235 | 8/2008 |
| JP | 2009-279438 | 12/2009 |
| JP | 2010-506681 | 3/2010 |
| JP | 2010-510011 | 4/2010 |
| JP | 2010-523181 | 7/2010 |
| JP | 2011-507668 | 3/2011 |
| JP | 2011-521744 | 7/2011 |
| JP | 2011-240159 | 12/2011 |
| JP | 2012-505066 | 3/2012 |
| JP | 2012-066767 | 4/2012 |
| JP | 2012-516737 | 7/2012 |
| JP | 2012-519028 A | 8/2012 |
| JP | 2013-506444 | 2/2013 |
| JP | 2013-069305 | 4/2013 |
| JP | 2013-075154 | 4/2013 |
| JP | 2013-537844 | 10/2013 |
| JP | 2014-500746 | 1/2014 |
| JP | 2014-502890 | 2/2014 |
| JP | 2014-503279 | 2/2014 |
| JP | 2014-506159 | 3/2014 |
| JP | 2014-507223 | 3/2014 |
| JP | 2014-515941 | 7/2014 |
| JP | 2014-516700 | 7/2014 |
| JP | 2014-516702 | 7/2014 |
| JP | 2014-521113 | 8/2014 |
| JP | 2014-4528787 | 10/2014 |
| JP | 2015-521920 | 8/2015 |
| JP | 2015-163208 | 9/2015 |
| JP | 2016-208611 | 12/2016 |
| JP | 2001-513371 | 9/2021 |
| KR | 10-2015-0125701 | 11/2015 |
| KR | B-10-1666755 | 10/2016 |
| PT | 3397321 | 10/2022 |
| RU | 2014-120469 | 11/2015 |
| WO | WO 2002/051471 | 7/2002 |
| WO | WO 2005/102416 | 11/2005 |
| WO | WO 2006/116997 | 11/2006 |
| WO | WO 2008/062025 | 5/2008 |
| WO | WO 2006/059597 | 6/2008 |
| WO | WO 2010/098927 | 9/2010 |
| WO | WO 2010/098931 | 9/2010 |
| WO | WO 2012/112347 | 8/2012 |
| WO | WO 2010/100883 | 9/2012 |
| WO | WO 2012/160157 | 11/2012 |

(56) References Cited

FOREIGN PATENT DOCUMENTS

| | | |
|---|---|---|
| WO | WO 2013/065055 | 5/2013 |
| WO | WO 2013/138830 | 9/2013 |
| WO | WO 2014/008393 | 1/2014 |
| WO | WO 2012/066767 | 5/2014 |
| WO | WO 2014/144096 | 9/2014 |
| WO | WO 2014/166915 | 10/2014 |
| WO | WO 2014/168205 | 10/2014 |
| WO | WO 2014/187812 | 11/2014 |
| WO | WO 2014/187813 | 11/2014 |
| WO | WO 2015/006430 | 1/2015 |
| WO | WO 2013/069305 | 4/2015 |
| WO | WO 2015/055640 | 4/2015 |
| WO | WO 2015/055642 | 4/2015 |
| WO | WO 2015/115326 | 8/2015 |
| WO | WO 2015/187797 | 12/2015 |
| WO | WO 2016/005421 | 1/2016 |
| WO | WO 2016/033507 | 3/2016 |
| WO | WO 2016/098060 | 6/2016 |
| WO | WO 2014/091765 | 1/2017 |
| WO | WO 2017/114906 | 7/2017 |
| WO | WO 2017/114907 | 7/2017 |
| WO | WO 2017/114908 | 7/2017 |
| WO | WO 2017/114909 | 7/2017 |
| WO | WO 2017/114910 | 7/2017 |
| WO | WO 2017/114911 | 7/2017 |
| WO | WO 2017/114912 | 7/2017 |
| WO | WO 2018/215516 | 11/2018 |
| WO | WO 2019/002534 | 1/2019 |
| WO | WO 2020/176319 | 9/2020 |
| WO | WO 2023/052487 | 4/2023 |

OTHER PUBLICATIONS

English Translation of Office Action dated Jul. 9, 2021, in corresponding Russian Application No. 2019140269.
English Translation of Office Action dated Jul. 30, 2021, in corresponding Russian Application No. 2020103216.
English Translation of Office Action dated Jun. 10, 2021, in corresponding Chinese Application No. 201880033657.4.
English translation of Office Action issued in Japanese Application No. 2019-565323, dated Jan. 5, 2022.
European Search Report for EP 15203132.4, dated Jun. 29, 2016.
European Search Report for EP 15203137.3, dated Jul. 1, 2016.
Partial European Search Report for EP15203168.8, dated Sep. 16, 2016.
International Search Report for PCT/EP2016/082861, dated Mar. 22, 2017.
International Preliminary Report on Patentability for PCT/EP2016/082861, dated Jul. 12, 2018.
International Search Report for PCT/EP2016/082856, dated Mar. 28, 2017.
International Preliminary Report on Patentability for PCT/EP2016/08285, dated Jul. 12, 2018.
International Search Report for PCT/EP2016/082860, dated May 3, 2017.
International Preliminary Report on Patentability for PCT/EP2016/082860, dated Jul. 12, 2018.
International Search Report for PCT/EP2016/082858, dated Mar. 24, 2017.
International Preliminary Report on Patentability for PCT/EP2016/082858, dated Jul. 12, 2018.
International Search Report for PCT/EP2016/082855, dated Mar. 24, 2017.
International Preliminary Report on Patentability for PCT/EP2016/082855, dated Jul. 12, 2018.
International Search Report for PCT/EP2016/082857, dated May 12, 2017.
International Preliminary Report on Patentability for PCT/EP2016/082857, dated Jul. 12, 2018.
International Search Report for PCT/EP2016/082859, dated Apr. 10, 2017.
International Preliminary Report on Patentability for PCT/EP2016/082859, dated Jul. 12, 2018.
International Search Report for PCT/EP2018/063460, dated Mar. 7, 2018.
International Preliminary Report on Patentability for PCT/EP2018/063460, dated Dec. 5, 2019.
International Search Report for PCT/EP2018/067532, dated Sep. 25, 2018.
International Preliminary Report on Patentability for PCT/EP2018/067532, dated Jan. 9, 2020.
English translation of Office Action issued in Japanese Application No. 2019-570894, dated Jan. 13, 2022.
English translation of Office Action issued in Chinese Application No. 201880033657, dated Feb. 23, 2022.
English translation of Office Action issued in Japanese Application No. 2021-116315, dated Sep. 2, 2022.
English translation of Office Action issued in Korean Application No. 10-2020-7000564, dated Oct. 17, 2022.
Office Action in Canadian Application No. 3,006,626, dated Dec. 19, 2022, in 5 pages.
Office Action in Canadian Application No. 3,006,616, dated Dec. 19, 2022, in 3 pages.
English translation of Office Action issued in Japanese Application No. JP 2022-074131, dated Apr. 28, 2023, in 2 pages.
English translation of Office Action issued in Japanese Application No. JP 2021-116315, dated Apr. 25, 2023, in 3 pages.
European Search Report for EP 18733296.0, dated Feb. 1, 2023, in 5 pages.
Office Action in Canadian Application No. 3,006,638, dated Jan. 17, 2023, in 4 pages.
Office Action in Canadian Application No. 3,006,627, dated Dec. 30, 2022, in 5 pages.
Office Action in Canadian Application No. 3,006,643, dated Jan. 4, 2023, in 7 pages.
Office Action in Canadian Application No. 3,006,622, dated Jan. 4, 2023, in 4 pages.
Office Action in New Zealand Application No. 742523, dated Feb. 27, 2023, in 3 pages.
Office Action in New Zealand Application No. 742538, dated Mar. 8, 2023, in 9 pages.
Office Action in New Zealand Application No. 742526, dated Mar. 13, 2023, in 8 pages.
Office Action in Australian Application No. 2018-294519, dated Mar. 10, 2023, in 3 pages.
Office Action in New Zealand Application No. 742526, dated Jul. 6, 2023, in 10 pages.
Office Action in Canadian Application No. 3,064,056, dated Jul. 11, 2023, in 5 pages.
English translation of Office Action issued in Japanese Application No. JP 2023-021789, dated Nov. 7, 2023, in 5 pages.
Hearing Notice dispatched on Dec. 29, 2023 in India Patent Application No. 201947041763.

* cited by examiner

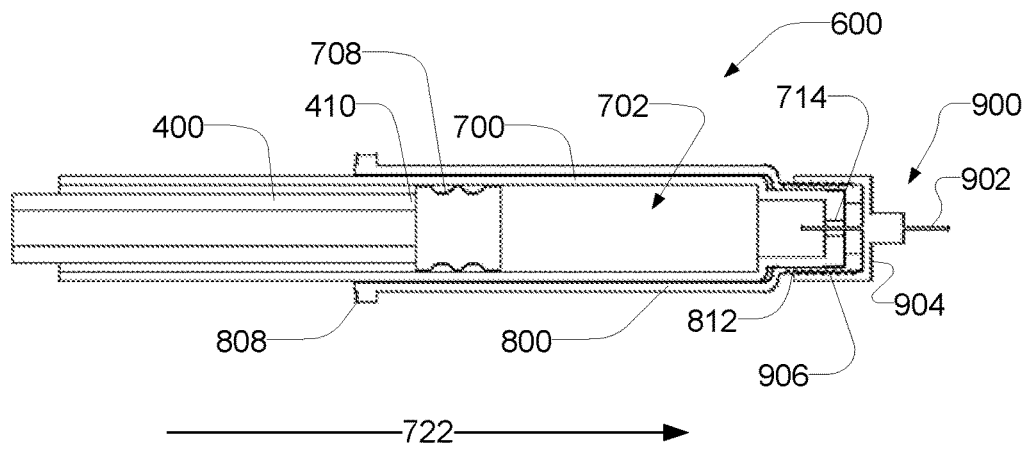
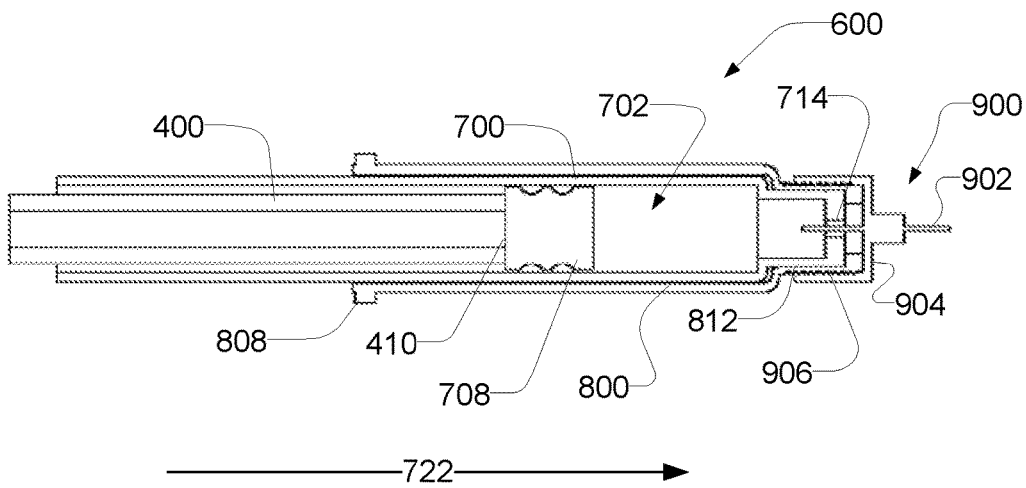
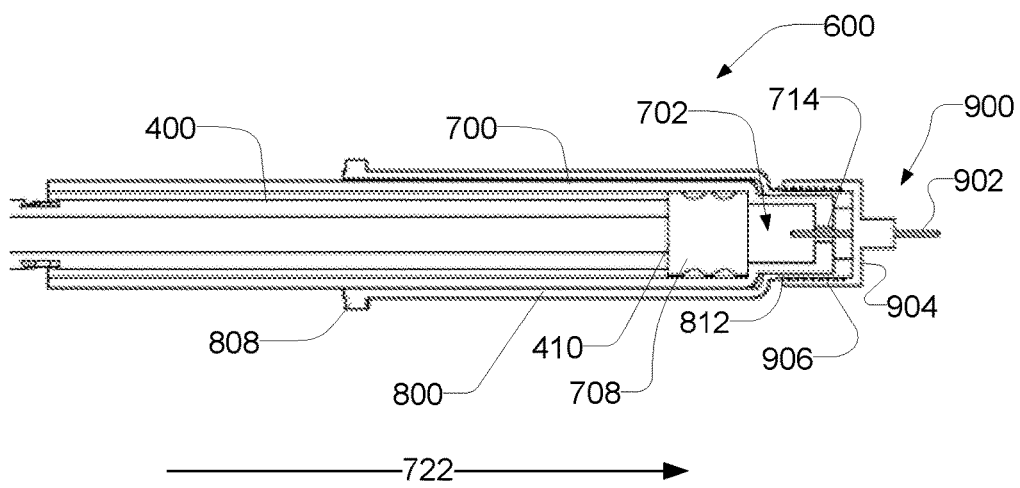

AUTO INJECTOR WITH ADAPTABLE AIR-SHOT MECHANISM

CROSS REFERENCE TO RELATED APPLICATIONS

This application is a continuation of U.S. application Ser. No. 16/060,606, filed Jun. 8, 2018, which is a U.S. National Phase Application of PCT International Application Number PCT/EP2016/082859, filed on Dec. 29, 2016, designating the United States of America and published in the English language, which is an International Application of and claims the benefit of priority to European Patent Application No. 15203171.2, filed on Dec. 30, 2015. The disclosures of the above-referenced applications are hereby expressly incorporated by reference in their entireties.

FIELD

The present disclosure relates to an auto injector, such as an electronic auto injector, a cartridge assembly for an auto injector, a system comprising an auto injector and a cartridge assembly, and a method for operating an auto injector.

INTRODUCTION/BACKGROUND

Hypodermic syringes are widely used to deliver fluids to the body. It is known to have hypodermic syringes applicable for manual operation. However, auto injectors, such as electronic auto injectors, have been developed and are widely used to aid the administering of fluid or medicaments to the body.

To avoid relying on users correctly performing certain tasks, it is of increasing interest that the auto injector automatically carries out as much as possible of the injection process.

It is generally known that air in a syringe should be depleted or minimized before injecting the medicament of the syringe. Injection of air may potentially cause problems such as air embolism e.g. in intra venous delivery. Thus, depletion or minimization of air in the syringe is usually performed before injecting the medicament. Also, for some injection systems minimized residual air trapped inside the syringe may positively influence resulting dose accuracy.

Depletion or minimization of air is usually done by performing an air-shot. An air-shot is generally performed by pointing the syringe upwards, such that the air is near the opening of the syringe, and performing an expelling action until medication is expelled. Thereby, the air is forced out of the syringe.

US 2009/299328 shows injection devices that can inject materials at predetermined, user selected injection rates, allowing the operator more control than a traditional syringe. The devices can allow mixing of more than one substance and/or reconstitution of a solid substance for injection.

SUMMARY

In spite of the known prior art, there is a need for an auto injector, such as an electronic auto injector, with an improved capability and accuracy of automatically performing an air-shot. The present disclosure provides an auto injector, a cartridge assembly, a system, and a method improving the capability of automatically performing an air-shot.

Accordingly, an auto injector for administering a medicament is disclosed. The auto injector comprises: a housing, a cartridge receiver, a code sensor, a drive module, and a processing unit.

The cartridge receiver is configured to receive a cartridge assembly comprising a cartridge and a cartridge code feature, the cartridge containing the medicament.

The code sensor is configured to read the cartridge code feature.

The drive module is coupled to move a plunger rod.

The processing unit is coupled to the code sensor and the drive module. The processing unit is configured to: receive from the code sensor a code signal indicative of the cartridge code feature; and control the drive module to move the plunger rod to a first plunger rod position, the first plunger rod position being based on the code signal.

The processing unit may further be configured to receive a trigger event, such as a trigger event after the plunger rod has been moved to the first plunger rod position; and control the drive module to move the plunger rod to a second plunger rod position following reception of the trigger event.

Also disclosed is a cartridge assembly for an auto injector, such as a cartridge assembly for the disclosed auto injector. The cartridge assembly comprising a cartridge and a cartridge code feature. The cartridge containing a medicament. The cartridge code feature being configured to be read by a code sensor of the auto injector for moving a plunger rod of the auto injector to a first plunger rod position based on the cartridge code feature.

Also disclosed is a system comprising a cartridge assembly, such as the disclosed cartridge assembly, and an auto injector, such as the disclosed auto injector. The cartridge assembly comprises a cartridge and a cartridge code feature, the cartridge containing a medicament. The auto injector comprises: a housing; a cartridge receiver configured to receive the cartridge assembly; a code sensor configured to read the cartridge code feature; a drive module coupled to move a plunger rod; and a processing unit coupled to the code sensor and the drive module. The processing unit being configured to: receive from the code sensor a code signal indicative of the cartridge code feature; and control the drive module to move the plunger rod to a first plunger rod position, the first plunger rod position being based on the code signal.

The processing unit may further be configured to: receive a trigger event, such as a trigger event after the plunger rod has been moved to the first plunger rod position; and control the drive module to move the plunger rod to a second plunger rod position following reception of the trigger event.

Also disclosed is a method for operating an auto injector comprising a plunger rod, such as the disclosed auto injector. The method comprising: receiving a cartridge assembly comprising a cartridge and a cartridge code feature, the cartridge containing a medicament; reading the cartridge code feature; and moving the plunger rod to a first plunger rod position, the first plunger rod position being based on the cartridge code feature.

The method may further comprise: receiving a trigger event, such as receiving a trigger event after the plunger rod has been moved to the first plunger rod position; and moving the plunger rod to a second plunger rod position following reception of the trigger event.

It is an advantage of the present disclosure that the air-shot may be adapted to the specific cartridge inserted into the auto injector, thereby leading to a more precise air-shot, which may prevent or at least reduce expelling of medicament during the air-shot.

It is an advantage of the present disclosure that the air-shot may be performed without expelling medicament through the tip of the needle, such as a needle of the syringe and/or a needle attached to the syringe. In some situations, it may be important or desired, that dosages are known accurately. Hence, it may be desirable that the amount of medicament in the syringe is fully injected into the patient and it is therefore an advantage that the air-shot may be performed automatically, and without expelling medicament through the tip of the needle.

Furthermore, medicament on the tip of a needle may provide patient discomfort upon insertion of the needle. And, especially for some medicaments, it may be undesirable to spill medicament, e.g. on the floor. It is thus a further advantage of performing the air-shot without expelling medicament from the tip of the needle that patient discomfort may be reduced.

It is a further advantage of the present disclosure that residual air trapped in the cartridge compartment together with drug to be injected may be minimized.

It is thus advantageous that the present disclosure may increase dosage accuracy, decrease patient discomfort, and/or avoid spilled medicament.

It is envisaged that any embodiments or elements as described in connection with any one aspect may be used with any other aspects or embodiments, mutatis mutandis.

The cartridge receiver may be configured to receive the cartridge and/or cartridge assembly through a cartridge receiver opening. Thus, the cartridge and/or cartridge assembly may be inserted in the cartridge receiver through the cartridge receiver opening.

The cartridge may comprise a cartridge compartment. The cartridge compartment may contain the medicament.

The cartridge may comprise a cartridge outlet, e.g. at a first cartridge end. The cartridge outlet may be configured for fluid communication with the compartment, e.g. at the first cartridge end. The cartridge may be configured to expel medicament through the cartridge outlet. The cartridge outlet may be configured to be coupled with a needle, such as a hypodermic needle, to provide the medicament to be expelled through the needle.

The cartridge assembly may comprise the needle, such as a needle assembly comprising the needle. The needle assembly may comprise a needle cover and/or a needle hub. The cartridge assembly may comprise a cartridge holder. The cartridge holder may be configured to engage with the needle assembly. The cartridge holder may provide for attachment of the needle assembly to the cartridge.

The cartridge may comprise a first stopper movable inside the cartridge compartment, e.g. towards the cartridge outlet, e.g. in a first stopper direction, such as towards the first cartridge end. For example, the medicament may be expelled through the cartridge outlet upon movement of the first stopper, e.g. in the first stopper direction and/or towards the cartridge outlet.

The cartridge may comprise a cartridge back face, e.g. at a second cartridge end, such as opposite the cartridge outlet. The cartridge back face may comprise a cartridge back end opening. The cartridge back end opening may provide access for the plunger rod to the first stopper.

The cartridge code feature may comprise one or more of a colour, a bar code, an RFID tag, an NFC tag, an identification number, and a QR code. For example, the cartridge code feature may comprise a colour and/or a sequence of colours.

The cartridge code feature may be positioned surrounding or partly surrounding a part of the cartridge compartment wherein a stopper, such as the first stopper, is initially positioned. Such position of the cartridge code feature may increase readability of the cartridge code feature, e.g. since the stopper may form a background for the cartridge code feature. The stopper, such as the first stopper may be a light colour, such as light grey or white. The stopper, such as the first stopper, may be a dark colour, such as dark blue, dark grey, or black. The stopper may form a dark background for the cartridge code feature. The stopper, such as the first stopper, may reduce reflection of light, e.g. to further increase readability of the cartridge code feature. The cartridge code feature being positioned at a part of the cartridge compartment wherein a stopper is positioned may avoid unnecessarily covering of visible area into the cartridge compartment, e.g. for purpose of visual inspection of the medicament.

The cartridge code feature may be positioned at a specific position on the cartridge, e.g. independently of the stopper(s), such as the first stopper. For example, the cartridge code feature may be positioned at a code distance from the second cartridge end. All cartridges may have their cartridge code features positioned at the same position, e.g. positioned at the code distance from the second cartridge end. Such uniform position of the cartridge code feature may decrease complexity, and decrease size, of the auto injector, as the cartridge code feature is read in the same position for all suitable cartridges.

The cartridge and the cartridge code feature may be manufactured as one element. For example, the cartridge code feature may be a certain form of the cartridge. Alternatively, the cartridge code feature may be attached to the cartridge, such as fastened, e.g. by glue, to the cartridge. For example, the cartridge code feature may be a colour code printed on the cartridge.

The cartridge code feature may be indicative of one or more cartridge specifications, such as medicament in the cartridge, concentration of medicament in the cartridge, viscosity of medicament in the cartridge, volume and/or mass of medicament in the cartridge, positions of stopper(s) in the cartridge compartment, etc. The cartridge code feature may be indicative of a position of the first stopper wherein air in the cartridge compartment is reduced, such as minimized and/or reduced to an amount appropriate for injection. The cartridge code feature may be indicative of the amount of medicament contained in the cartridge. The cartridge code feature may be indicative of a specific type of cartridge, such as an ID number of the specific type of cartridge. The auto injector, such as the processing unit of the auto injector, may be configured to determine one or more cartridge specifications based on an ID number, e.g. by table lookup. The cartridge code feature may be indicative of a suitable speed of stopper movement. For example, the cartridge code feature may be indicative of the speed of movement of the plunger rod to the first plunger rod position and/or to the second plunger rod position and/or to a third plunger rod position. The cartridge code feature may be indicative of a suitable speed of stopper movement, such as stopper movement in different phases of movement, such as during air-shot and/or injection, such as towards the first plunger rod position and/or towards the second plunger rod position.

The cartridge code feature may be indicative of one or more delays, such as time delays, e.g. comprising a delay to elapse before initiating a movement of the plunger rod and/or first stopper and/or comprising a delay to elapse between completion of one movement of the plunger rod and/or first stopper and initiation of another movement of the plunger rod and/or first stopper.

The one or more delays may comprise a first delay. The first delay may be required to elapse before the plunger rod is moved to the first plunger rod position. For example, the first delay may be required to elapse before initiation of movement of the plunger rod to the first plunger rod position. For example, the first delay may be chosen to allow the medicament to settle before initiating the air-shot, e.g. after a reconstitution or mixing of the medicament, which may cause a foaming effect in the medicament. The first delay may allow the foaming effect in the medicament to settle.

The one or more delays may comprise a second delay. The second delay may be required to elapse before the plunger rod is moved to the second plunger rod position. For example, the second delay may be required to elapse after completion of movement of the plunger rod to the first plunger rod position and before initiation of movement of the plunger rod to the second plunger rod position.

The auto injector and/or the processing unit may be configured to determine the first delay and/or the second delay based on the code signal.

The auto injector may be an electronic auto injector. The auto injector may comprise a battery. The housing may accommodate the battery. The battery may be a rechargeable battery. For example, the battery may be a Li-ion battery or a NiCd battery or a NiMH battery. The battery may be configured to be charged by connection of a charger.

The drive module is coupled to move, such as actuate, such as advance, the plunger rod. The drive module may comprise one or more electrical elements. The drive module may be configured to receive electrical power from the battery. The drive module may be electrically connected to the battery for receiving electrical power. The drive module may be accommodated by the housing. The drive module may comprise a motor, such as an electro-mechanical motor, such as a DC motor, e.g. a DC motor with or without brushes. The drive module may comprise a solenoid motor. The drive module may comprise a shape memory metal engine. The drive module may comprise an arrangement of springs configured to actuate the plunger rod. The drive module may comprise a pressurized gas configured to actuate the plunger rod.

The plunger rod may be configured to advance a first stopper, such as the first stopper of the cartridge. The advancement of the first stopper may be to expel medicament from the cartridge compartment through the cartridge outlet and/or to expel air from the cartridge compartment through the cartridge outlet. The plunger rod may be movable between a retracted plunger rod position and an extended plunger rod position.

The auto injector, such as the processing unit of the auto injector, may be configured to receive a trigger event, such as a trigger event indicating that the user initiates injection of the medicament. The auto injector, such as the processing unit of the auto injector, may be configured to receive the trigger event after the plunger rod has been moved to the first plunger rod position.

The trigger event may be used to start an injection sequence of the auto injector. The auto injector, such as the processing unit of the auto injector, may control the drive module to move the plunger rod to a second plunger rod position, such as a position wherein the medicament is injected and/or ejected from the cartridge compartment, following reception of the trigger event. The trigger event may initiate the movement of the plunger rod to expel medicament from the cartridge compartment through the cartridge outlet.

The trigger event may, for example, be an effect of a push of a button, an effect of an elapsed timeout, and/or an effect of a predetermined user behaviour. The trigger event may be indicative of the auto injector being pressed against the injection site.

The auto injector may comprise an ejection sensor, e.g. configured to detect the ejection, such as the expelling, of medicament and/or air in the cartridge compartment. The ejection sensor may be configured to detect and/or determine the position of the plunger rod and/or the position of the first stopper. The ejection sensor may be configured to detect conditions indicative of the position of the plunger rod and/or the position of the first stopper. The ejection sensor may be configured to provide an ejection sensor signal. The ejection sensor signal may be indicative of the position of the plunger rod and/or the first stopper.

The ejection sensor may comprise a tachometer, e.g. a tachometer of the drive module. The tachometer may be configured to count the revolutions of the drive module, such as a motor of the drive module, such as the revolutions of the drive module from a set point, such as a point wherein the position of the plunger rod is known, such as a fully retracted position of the plunger rod. The count of revolutions of the drive module may be used to determine the actual position of the plunger rod, such as the first plunger rod position and/or the second plunger rod position.

The processing unit may be coupled to the ejection sensor, such as to the tachometer of the ejection sensor. The processing unit may receive from the ejection sensor a first ejection sensor signal, such as a tachometer signal, indicative of the count of revolutions of the drive module. The processing unit may determine the position of the plunger rod based on the first ejection sensor signal. The processing unit may receive a second ejection sensor signal, e.g. from the ejection sensor, indicative of the plunger rod being in a known position, such as a fully retracted position. The processing unit may determine the position of the plunger rod based on the first ejection sensor signal and the second ejection sensor signal.

The ejection sensor signal may include the first ejection sensor signal and/or the second ejection sensor signal.

The first plunger rod position may be selected to expel air from the cartridge. For example, the first plunger rod position may be selected to position the first stopper in a position wherein air in the cartridge compartment is reduced, such as minimized and/or reduced to an amount appropriate for injection. The first plunger rod position may be a position of the plunger rod wherein the air-shot has been completed. The first plunger rod position may be a position wherein air has been expelled from the cartridge compartment, such as wherein the first stopper is in a position wherein air has been expelled from the cartridge compartment. The first plunger rod position may be positioned between the retracted plunger rod position and the extended plunger rod position. The first plunger rod position may be based on the cartridge code feature. For example, the processing unit may be configured to determine the first plunger rod position based on the code signal.

The second plunger rod position may be selected to expel medicament from the cartridge. For example, the second plunger rod position may be selected to position the first stopper in a position wherein medicament in the cartridge compartment is reduced, such as minimized, such as in a position closest to the cartridge outlet. The second plunger rod position may be positioned between the first plunger rod position and the extended plunger rod position. The second plunger rod position may be the extended plunger rod position. The second plunger rod position may be based on the cartridge code feature. For example, the processing unit may be configured to determine the second plunger rod position based on the code signal.

The third plunger rod position may be selected to mix a plurality of components of the medicament, e.g. to reconstitute the medicament. For example, the third plunger rod position may be selected to position the first stopper in a position wherein a first medicament component is mixed with a second medicament component. The third plunger rod position may be positioned between the retracted plunger rod position and the first plunger rod position. The third plunger rod position may be based on the cartridge code feature. For example, the processing unit may be configured to determine the third plunger rod position based on the code signal.

A fourth plunger rod position may be configured to advance the first stopper to a position before mixing of the plurality of components of the medicament is commenced. The fourth plunger rod position may be positioned between the retracted plunger rod position and the third plunger rod position. The fourth plunger rod position may be based on the cartridge code feature. For example, the processing unit may be configured to determine the fourth plunger rod position based on the code signal.

Movements of the plunger rod may be separated and/or preceded and/or followed by the one or more delays.

The auto injector may comprise a user interface, such as a user interface allowing user input and/or provide visual and/or audible output to the user.

The auto injector may comprise a trigger member, such as a trigger member of the user interface. The trigger event may comprise activation of the trigger member. The trigger member may be a button of the user interface, such as a push-button. Alternatively or additionally, the trigger member may be a contact member, such as a skin sensor. The contact member may be configured to be pressed against the injection site for activation. For example, to activate the injection of the medicament. The contact member may be surrounding the cartridge outlet and/or the intended position of the cartridge outlet, such as the cartridge receiver opening. The contact member may be configured to activate a contact sensor when pressed against the skin, e.g. when moved relative to the housing. The contact sensor may be configured to transmit the trigger event. The processing unit may be coupled to the contact sensor. The processing unit may be configured to receive the trigger event from the contact sensor.

The auto injector may comprise an orientation sensor. The orientation sensor may be configured to detect an orientation of the cartridge and/or an orientation indicative of the orientation of the cartridge, such as an orientation of the auto injector. The orientation sensor may be configured to detect the direction of gravity, and/or if the direction of gravity is within a certain range of a predetermined direction. The orientation sensor may comprise an accelerometer. The orientation sensor may comprise a plurality of accelerometers, such as three accelerometers, such as three accelerometers arranged to detect acceleration in three dimensions, such as a three-dimensional accelerometer. The orientation sensor may comprise a tilt sensor, a tri-axial accelerometer, a single axis accelerometer, a magnetometer and/or any combination thereof, and the orientation sensor may provide a measure of roll, pitch and azimuth, a measure of acceleration and/or tilt in one or more directions.

The orientation sensor may be configured to detect if the cartridge is in a predetermined orientation. The orientation sensor may be configured to detect if the orientation of the auto injector is indicative of the cartridge being in the predetermined orientation. The predetermined orientation may be a vertical orientation. The predetermined orientation may be an orientation within 45 degrees of vertical, such as within 30 degrees of vertical. The predetermined orientation may be an orientation wherein the cartridge is orientated such that a longitudinal axis of the cartridge is within 45 degrees of vertical, such as within 30 degrees of vertical, and wherein the cartridge outlet is above the cartridge compartment, such as in a vertical position above the cartridge compartment.

The processing unit may be coupled to the orientation sensor. The processing unit may be configured to receive from the orientation sensor an orientation signal indicative of the orientation of the cartridge when received in the cartridge receiver, and/or of the auto injector. The processing unit may be configured to control the drive module to move the plunger rod to the first plunger rod position based on the orientation signal. For example, the processing unit may be configured to control the drive module to move the plunger rod to the first plunger rod position only if the orientation signal indicates that a tilt angle between vertical and a longitudinal axis extending along the cartridge is within 45 degrees, such as within 30 degrees, of vertical and/or if the cartridge outlet is in a vertical position above the cartridge compartment.

The auto injector may comprise a code sensor, such as a code sensor configured to read the cartridge code feature. The code sensor may be configured to transmit a code signal indicative of the cartridge code feature. The code sensor may be configured to read the cartridge code feature in a plurality of positions. The cartridge code sensor may be movable. The cartridge code sensor may comprise a plurality of sensors, such as a plurality of transmitters and/or receivers.

The auto injector, such as the processing unit of the auto injector, may be configured to move the plunger rod based on the code signal and/or the cartridge code feature. The auto injector, such as the processing unit of the auto injector, may be configured to move the plunger rod to the first plunger rod position based on the code signal and/or the cartridge code feature. The first plunger rod position, e.g. wherein the air-shot is completed, may be determined based on the cartridge assembly, such as on the cartridge code feature, such as on the cartridge code signal. The movement of the plunger rod and/or the first stopper may be based on the cartridge assembly, e.g. on the cartridge code feature. Thus, the air-shot may be performed with reduced or no expelling of medicament, thereby increasing dosage accuracy and/or reduce patient discomfort.

Movement of the plunger rod may comprise movement having a plunger rod speed, such as a first plunger rod speed and/or a second plunger rod speed. The plunger rod speed may be based on the position of the plunger rod. The plunger rod may be moved to the first plunger rod position with a first plunger rod speed. The plunger rod may be moved to the second plunger rod position, such as from the first plunger rod position, with a second plunger rod speed. The second plunger rod speed may be faster or slower than the first plunger rod speed.

The plunger rod may be moved to the third plunger rod position with a third plunger rod speed. The plunger rod may be moved to the fourth plunger rod position with a fourth plunger rod speed.

The first plunger rod speed and/or the second plunger rod speed and/or the third plunger rod speed and/or the fourth plunger rod speed may be based on a cartridge specification, such as on the cartridge code feature, such as on the code signal. The processing unit may be configured to determine the first plunger rod speed and/or the second plunger rod speed and/or the third plunger rod speed and/or the fourth plunger rod speed, based on the code signal.

The processing unit may be configured to control the drive module to move the plunger rod to the first plunger rod position with the first plunger rod speed. The processing unit may be configured to control the drive module to move the plunger rod to the second plunger rod position, such as from the first plunger rod position, with the second plunger rod speed.

The code sensor may comprise an optical sensor. The code sensor may comprise an optical sensor comprising a transmitter and a receiver, such as a light transmitter and a light receiver. The code sensor may be configured to read the cartridge code feature. The code sensor may be configured to read QR codes, bar codes, colour codes, and/or any combination hereof.

The auto injector may comprise a temperature sensor. The temperature sensor may be configured to provide a temperature signal, such as a temperature signal indicative of the temperature of the auto injector and/or of the cartridge and/or of the medicament. The temperature sensor may comprise an infrared sensor, such as an optical infrared sensor. The temperature sensor and the code sensor may be the same sensor. For example, an optical infrared sensor for sensing temperature may be the same physical sensor as an optical sensor for reading the cartridge code feature.

The processing unit may be coupled to the temperature sensor. The processing unit may be configured to receive the temperature signal.

Movement of the plunger rod, e.g. to the first plunger rod position and/or to the second plunger position, may be based on the temperature of the auto injector and/or of the cartridge and/or of the medicament, e.g. on the temperature signal.

The auto injector, such as the processing unit, may be configured to control the drive module based on the temperature signal. For example, the processing unit may be configured to control the drive module to move the plunger rod to the first plunger rod position and/or to the second plunger rod position based on the temperature signal.

The first plunger rod speed and/or the second plunger rod speed and/or the third plunger rod speed and/or the fourth plunger rod speed may be determined based on temperature, such as the temperature of the auto injector and/or of the cartridge and/or of the medicament, e.g. on the temperature signal. The first plunger rod position and/or the second plunger rod position and/or the third plunger rod position and/or the fourth plunger rod position may be determined based on the temperature signal and/or temperature, such as the temperature of the auto injector and/or of the cartridge and/or of the medicament. For example, the volume of the medicament may be dependent on temperature, and therefore, the air-shot may be more precisely controlled when taking into account the temperature. Thus, the air-shot may be performed with reduced or no expelling of medicament, thereby, for example, increasing dosage accuracy and/or reducing patient discomfort.

The processing unit may be coupled to the orientation sensor, the code sensor, the ejection sensor, and/or the temperature sensor. The processing unit may be configured to receive the orientation signal, the code signal, the ejection sensor signal, and/or the temperature signal. The processing unit may be configured to control the drive module to move the plunger rod to the first plunger rod position and/or the second plunger rod position based on the orientation signal, the code signal, the ejection sensor signal, and/or the temperature signal.

The auto injector may comprise a cartridge sensor. The cartridge sensor may be configured to detect reception of a cartridge assembly in the auto injector and/or in the cartridge receiver of the auto injector. The cartridge sensor may provide a cartridge sensor signal indicative of reception of a cartridge assembly. The code sensor and the cartridge sensor may be the same sensor, e.g. the code sensor may be configured to detect reception of a cartridge assembly and subsequently read the cartridge code feature.

The processing unit may be coupled to the cartridge sensor. The processing unit may be configured to receive the cartridge sensor signal. The processing unit may be configured to control the drive module based on the cartridge sensor signal. For example, the processing unit may be configured to control the drive module to start movement of the plunger rod if a cartridge assembly is received, and/or only if a cartridge assembly is received.

The auto injector may comprise a needle sensor. The needle sensor may be configured to detect a needle, and/or a needle assembly, and/or a needle cover of a needle assembly, of the cartridge assembly, e.g. when the cartridge assembly is received in the auto injector and/or in the cartridge receiver of the auto injector. The needle sensor may provide a needle signal indicative of the presence of a needle, and/or a needle assembly, and/or a needle cover of a needle assembly.

The processing unit may be coupled to the needle sensor. The processing unit may be configured to receive the needle signal. The processing unit may be configured to control the drive module based on the needle signal. For example, the processing unit may be configured to control the drive module to start movement of the plunger rod only if a needle is present, and/or only if a needle cover is not present.

The auto injector may comprise a resistance sensor. The resistance sensor may be configured to detect resistance against movement of the plunger rod. The resistance sensor may be configured to detect resistance against movement of the plunger rod based on measurements of the drive module. For example, the resistance sensor may be configured to detect the electrical current of a motor of the drive module. The resistance sensor may be configured to provide a resistance signal indicative of resistance against movement of the plunger rod.

The processing unit may be coupled to the resistance sensor. The processing unit may be configured to receive the resistance signal. The processing unit may be configured to determine the resistance against movement of the plunger rod based on the resistance signal. The processing unit may be configured to control the drive module based on the resistance signal. For example, the processing unit may be configured to control the drive module to adjust movement of the plunger rod based on the resistance signal. For example, the processing unit may be configured to control the drive module to start, stop or continue movement of the plunger rod based on the resistance signal.

BRIEF DESCRIPTION OF THE FIGURES

A more detailed description follows below with reference to the drawing, in which.

FIGS. 6A, 6B, and 6C schematically illustrates an exemplary cartridge and a plunger rod in exemplary positions;

DETAILED DESCRIPTION

Figure 1:
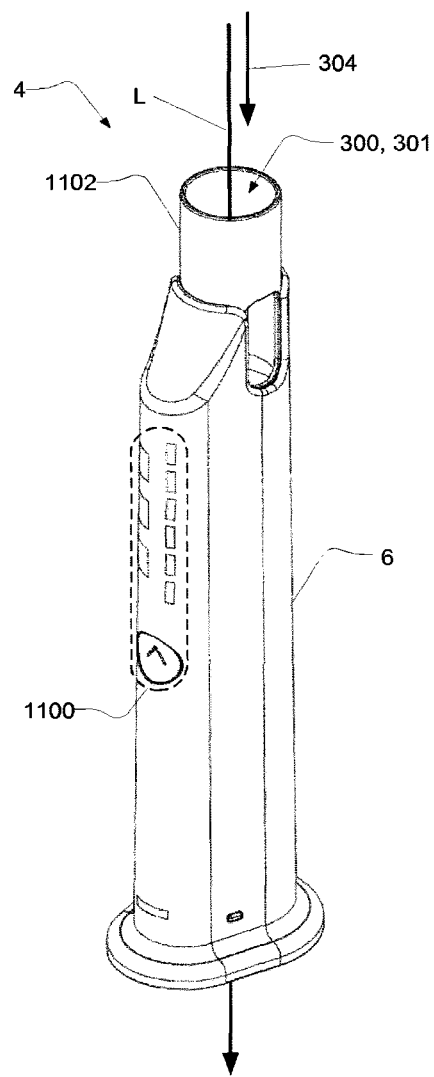
FIG. 1 illustrates an exemplary auto injector.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates an exemplary auto injector 4. The auto injector 4 may be configured for administering a medicament. The auto injector 4 may be an electronic auto injector.

The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis L.

The auto injector 4 may comprise a user interface 1100, as illustrated. The auto injector 4 comprises a trigger member, such as the contact member 1102. The contact member 1102 may be configured to be pressed against an injection site. The contact member 1102 may be movable in the cartridge receiving direction 304, relative to the housing 6, if pressed against the injection site. The contact member 1102 may be part of the user interface 1100.

Figure 2:
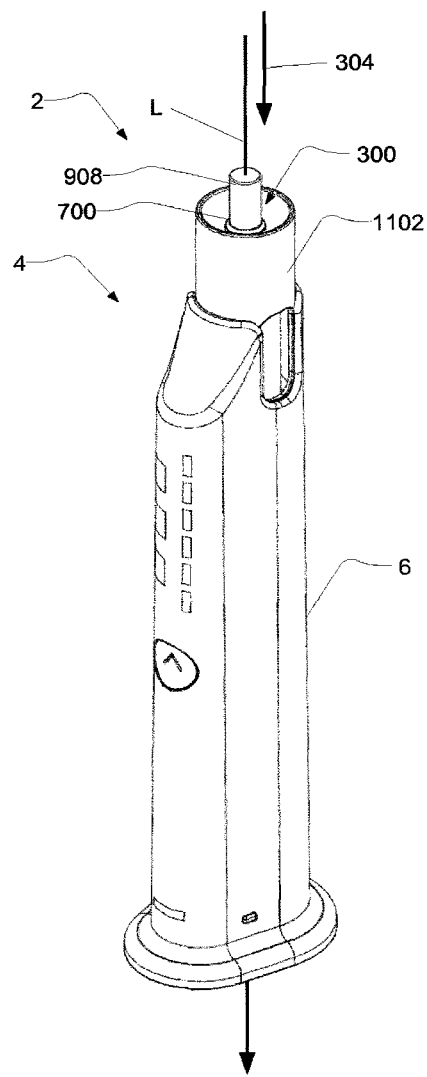
FIG. 2 illustrates an exemplary auto injector with a cartridge.

FIG. 2 illustrates an exemplary system 2. The system 2 comprises an auto injector 4, as described in relation to FIG. 1, and an exemplary cartridge 700 received in the cartridge receiver 300. The cartridge 700 is shown with a needle cover 908. The needle cover 908 extending out of the contact member 1102 to allow removal of the needle cover 908 from the cartridge 700.

Figure 3:
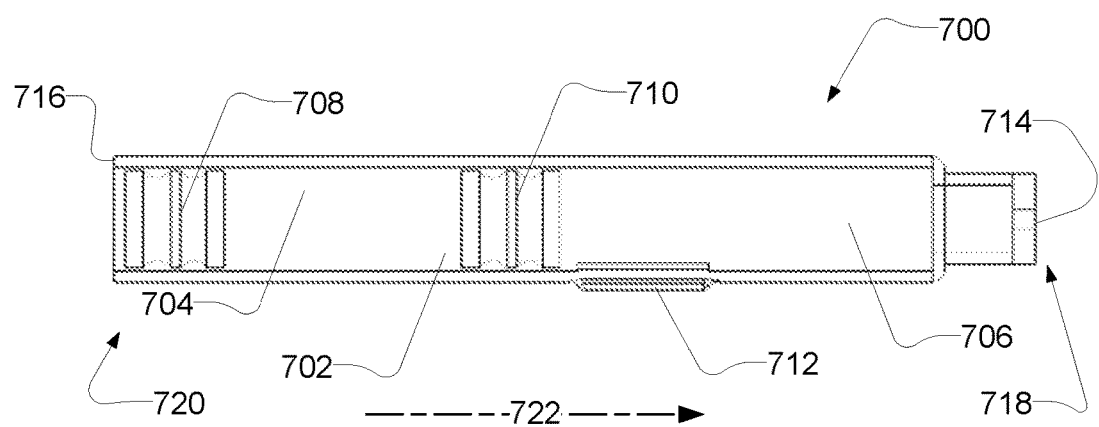
FIG. 3 schematically illustrates an exemplary cartridge.

FIG. 3 schematically illustrates an exemplary cartridge 700, such as a cartridge 700 being configured to be received in the cartridge receiver of an auto injector, such as the auto injector described in relation to previous figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at the first cartridge end 718. The cartridge 700 may be configured to expel medicament through the cartridge outlet 714.

The cartridge 700 comprises a first stopper 708 movable inside the cartridge compartment 702, e.g. in a first stopper direction 722, e.g. towards the first cartridge end 718. For example, the medicament may be expelled through the cartridge outlet 714 upon movement of the first stopper 708 in the first stopper direction 722. The cartridge comprises a cartridge back face 716 at the second cartridge end 720. The cartridge back face 716 comprises a cartridge back end opening for providing access to the first stopper 708 for a plunger rod.

As illustrated, the cartridge 700 may be a dual chamber cartridge. The cartridge comprises a second stopper 710 movable inside the cartridge compartment 702, e.g. in the first stopper direction 722, e.g. towards the first cartridge end 718. The cartridge compartment 702 comprises a first cartridge subcompartment 704 and a second cartridge subcompartment 706. The first cartridge subcompartment 704 is between the first stopper 708 and the second stopper 710. The second cartridge subcompartment 706 is between the second stopper 710 and the cartridge outlet 714. The cartridge comprises a bypass section 712 for providing fluid communication between the first cartridge subcompartment 704 and the second cartridge subcompartment 706. The bypass section 712 provides fluid communication between the first cartridge subcompartment 704 and the second cartridge subcompartment 706 when the second stopper 710 is positioned in the bypass section 712.

FIGS. 4A-4D schematically illustrates an exemplary cartridge assembly 600. The cartridge assembly 600 comprises an exemplary cartridge 700 and an exemplary cartridge code feature 1000. The cartridge 700 has a first cartridge end 718 and a second cartridge end 720. The first stopper direction 722 is from the second cartridge end 720 to the first cartridge end 718. The cartridge code feature 1000 is positioned near the second cartridge end 720, e.g. closer to the second cartridge end 720 than the first cartridge end 718. In another exemplary cartridge assembly, the cartridge code feature 1000 may be positioned near the first cartridge end 718.

FIGS. 4A-4D illustrates different types of exemplary cartridge code features 1000.

Figures 4A, 4B, 4C, 4D:
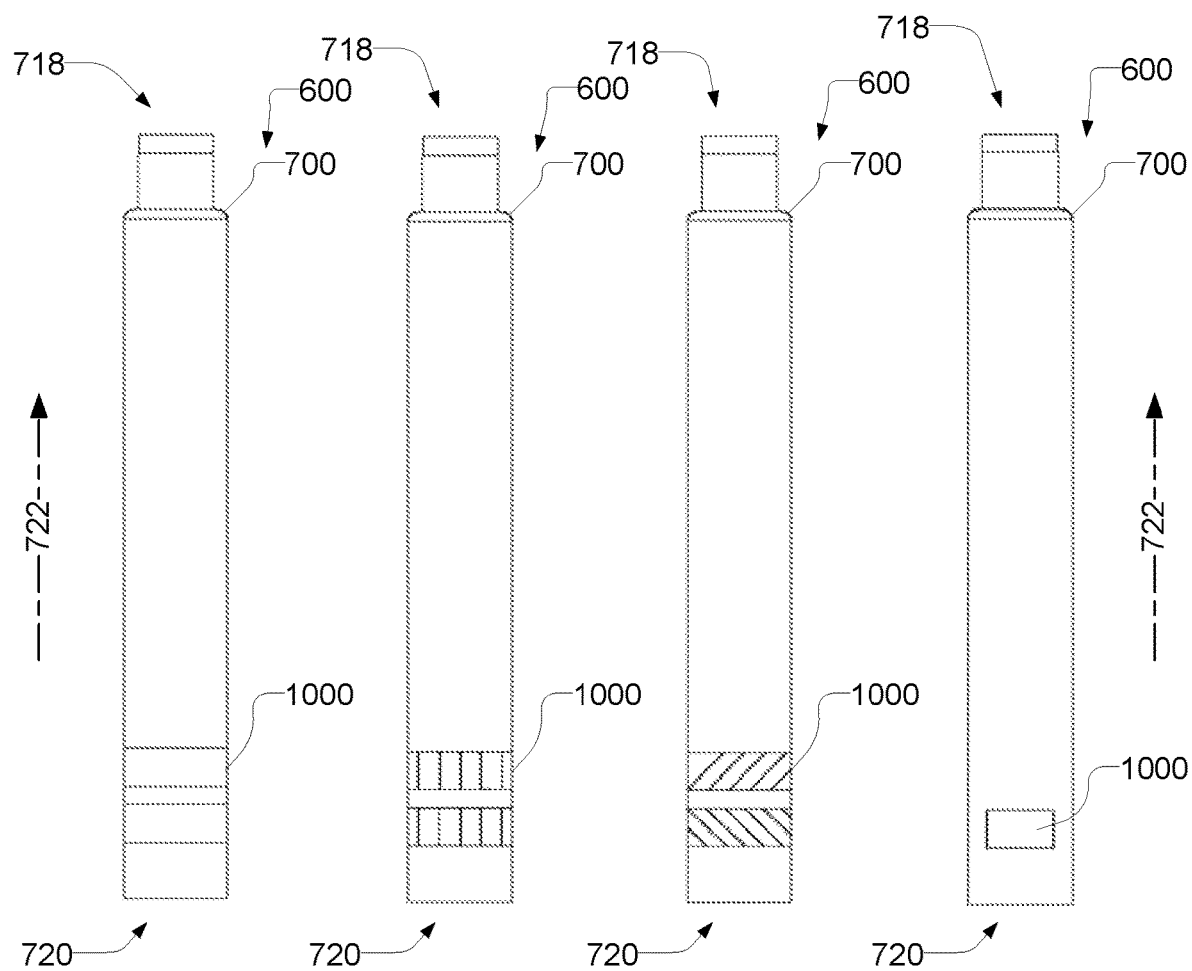
FIGS. 4A, 4B, 4C, and 4D schematically illustrates an exemplary cartridge with exemplary cartridge code features.

FIG. 4A illustrates an exemplary cartridge assembly 600, wherein the cartridge code feature 1000 comprises two strips. The two strips may be coloured, e.g. differently coloured. The combination and/or sequence of colours may be indicative of a code of the cartridge code feature 1000.

FIG. 4B illustrates an exemplary cartridge assembly 600, wherein the cartridge code feature 1000 comprises bar codes. The cartridge code feature 1000 may comprise one or more bar codes. The bar code may be indicative of a number indicative of a code of the cartridge code feature 1000.

FIG. 4C illustrates an exemplary cartridge assembly 600, wherein the cartridge code feature 1000 comprises differently grated strips. For example, as illustrated, the cartridge code feature 1000 may comprise two strips wherein the first strip is grated at 45 deg., and the second strip is grated at −45 deg. The grating, and/or the grating of the strips relative to each other, may be indicative of a code of the cartridge code feature 1000.

FIG. 4D illustrates an exemplary cartridge assembly 600, wherein the cartridge code feature 1000 comprises an electromagnetically readable tag, such as an RFID tag or an NFC tag. The electromagnetically readable tag may contain data that is indicative of a code of the cartridge code feature 1000.

Figure 5:
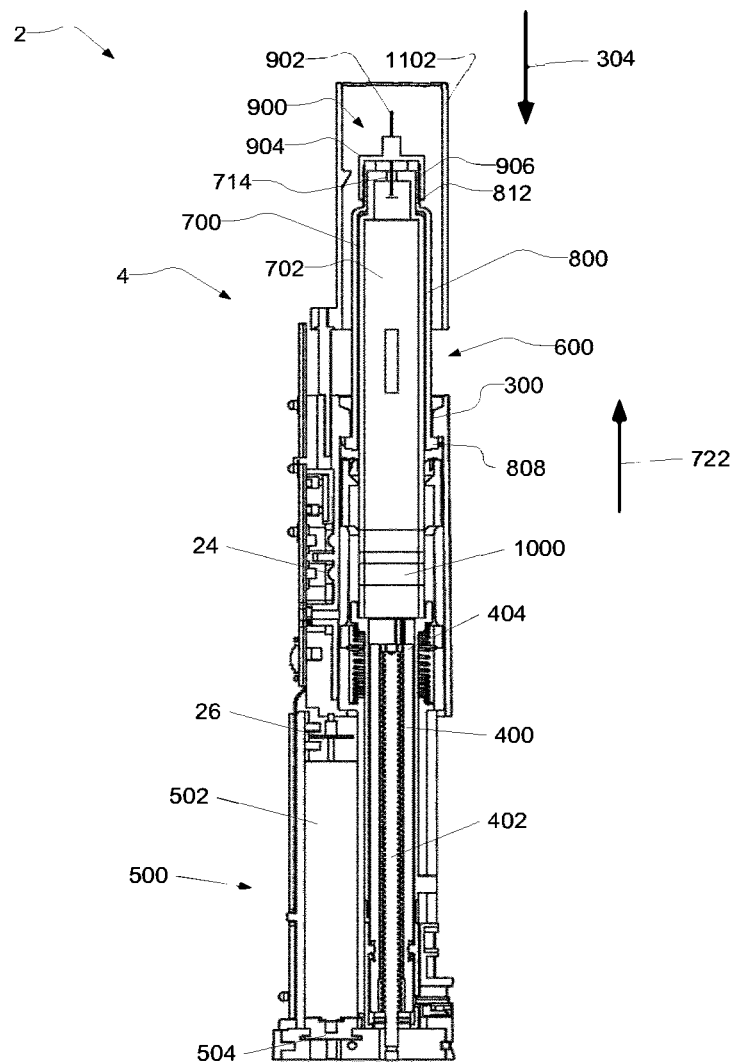
FIG. 5 schematically illustrates an exemplary auto injector with a cartridge.

FIG. 5 illustrates an exemplary system 2. The system 2 comprises an auto injector 4, as described, for example, in relation to FIG. 1, and an exemplary cartridge assembly 600. The cartridge assembly 600 comprises a cartridge 700 with a cartridge compartment 702, a needle assembly 900, and a cartridge code feature 1000. The cartridge assembly 600 is received in the auto injector 4.

The cartridge assembly 600 comprises a cartridge holder 800. The cartridge holder 800 is configured for retention of the cartridge 700 in the cartridge receiver 300 of the auto injector 4. The cartridge holder 800 comprises a cartridge retention member 808. The cartridge retention member 808 engages with the cartridge receiver 300 for reception of the cartridge 700 and the cartridge assembly 600 in the cartridge receiver 300.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700. The cartridge outlet 714 may be blocked by a resilient sealing being penetrated by the needle 902, when the needle assembly 900 is attached to the cartridge 700.

The auto injector 4 comprises a code sensor 24 configured to read the cartridge code feature 1000. When the cartridge assembly 600 is inserted, as shown, the cartridge code feature 1000 is lined up with the code sensor 24.

The auto injector 4 comprises a plunger rod 400. The plunger rod 400 is configured to advance a first stopper of the cartridge 700. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper of the cartridge 700, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400

Although the example shown comprises a motor 502, which may be an electro-mechanical motor, it will be readily understood that the auto injector 4 may be realised having an alternative drive module, such as comprising a solenoid motor, a shape memory metal engine, an arrangement of springs and/or a pressurized gas configured to actuate the plunger rod 400.

The auto injector 4 comprises an ejection sensor 26, such as a plunger rod position sensor. The ejection sensor 26 is configured to detect the position of the plunger rod 400. In the illustrated example, the ejection sensor 26 comprises a tachometer configured to count/detect the revolutions of the motor 502. Thus, the position of the plunger rod 400 may be determined. The ejection sensor 26 may, based on the detection of the position of the plunger rod 400, detect the expelling of medicament and/or air in the cartridge compartment. The position of the plunger rod 400 is indicative of the position of the first stopper of the cartridge 700.

FIGS. 6A-6C schematically illustrates an exemplary cartridge assembly 600 and a plunger rod 400 in exemplary positions.

The cartridge assembly 600 comprises a cartridge 700, a cartridge holder 800, and a needle assembly 900.

The cartridge 700 comprises a cartridge compartment 702, a first stopper 708 and a cartridge outlet 714. The cartridge compartment 702 is configured for containing a medicament (not shown). The cartridge 700 shown in FIGS. 6A-6C is a single chamber cartridge. However, it may be a dual chamber cartridge as, for example, explained in relation to FIG. 3.

The cartridge holder 800 comprises a cartridge retention member 808. The cartridge retention member 808 is configured for engagement with a cartridge receiver of the auto injector. The cartridge holder 800 comprises a needle assembly coupling portion 812. The needle assembly coupling portion 812 is configured for engagement with a cartridge holder coupling portion 906 of the needle assembly 900. The needle assembly coupling portion 812 allows attachment of a needle to the cartridge 700.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700.

FIG. 6A shows the first stopper 708 in an exemplary initial stopper position, and the plunger rod 400 in an exemplary initial plunger rod position. The plunger rod 400 is moved towards the cartridge outlet 714, e.g. in the first stopper direction 722, such that a plunger rod front end 410 of the plunger rod 400 abuts the first stopper 708.

FIG. 6B shows the first stopper 708 in an exemplary first stopper position, and the plunger rod 400 in an exemplary first plunger rod position. Compared to FIG. 6A, the plunger rod 400 has moved towards the cartridge outlet 714, e.g. in the first stopper direction 722, to the first plunger rod position. The first stopper 708 has moved to the first stopper position by the movement of the plunger rod 400. The first stopper 708 has been pushed by the plunger rod front end 410 of the plunger rod 400.

The first stopper position and/or the first plunger rod position may have been determined by a cartridge code feature (see FIGS. 4A-4D), of the cartridge assembly 600.

The first stopper position and/or the first plunger rod position may be the position of the first stopper 708 and/or the plunger rod 400 after completion of an air-shot. Thus, the first stopper position and/or the first plunger rod position may be the position of the first stopper 708 and/or the plunger rod 400 wherein air in the cartridge compartment 702 has been expelled, e.g. through the cartridge outlet 714 and/or the needle 902.

FIG. 6C shows the first stopper 708 in an exemplary second stopper position, and the plunger rod 400 in an exemplary second plunger rod position. Compared to FIG. 6B, the plunger rod 400 has moved towards the cartridge outlet 714, e.g. in the first stopper direction 722, to the second plunger rod position. The first stopper 708 has moved to the second stopper position by the movement of the plunger rod 400. The first stopper 708 has been pushed by the plunger rod front end 410 of the plunger rod 400.

The second stopper position and/or the second plunger rod position may be the position of the first stopper 708 and/or the plunger rod 400 after completion of ejection of medicament, such as after completion of injection of medicament. Thus, the second stopper position and/or the second plunger rod position may be the position of the first stopper 708 and/or the plunger rod 400 wherein medicament in the cartridge compartment 702 has been expelled, e.g. through the cartridge outlet 714 and/or the needle 902.

Figure 7:
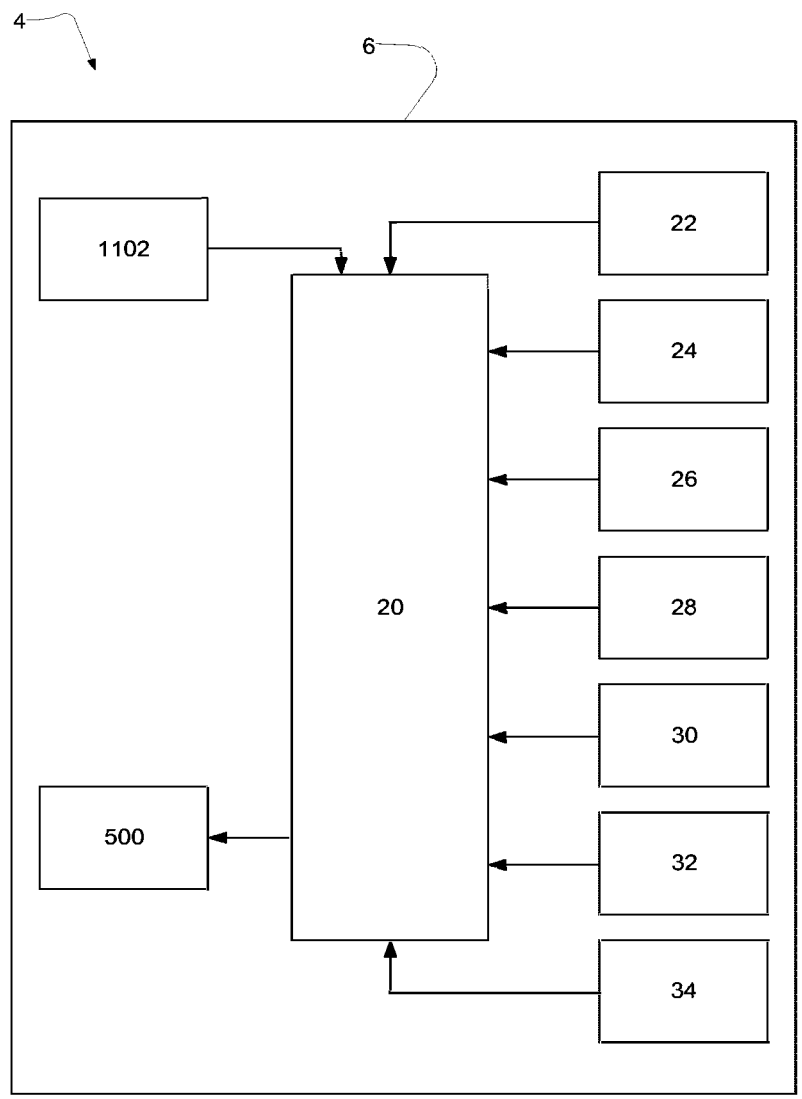
FIG. 7 shows a block diagram of an exemplary auto injector.

FIG. 7 shows a block diagram of an exemplary auto injector 4. The auto injector comprises a plurality of sensors 22, 24, 26, 28, 30, 32, 34, a processing unit 20, a drive module 500, and a trigger member 1102. The sensors 22, 24, 26, 28, 30, 32, 34 are coupled to the processing unit 20. The trigger member 1102 is coupled to the processing unit 20. The processing unit is coupled to the drive module 500.

The processing unit 20 receives signals from the sensors 22, 24, 26, 28, 30, 32, 34 and the trigger member 1102. The processing unit 20 is configured to control the drive module 500. The processing unit 20 may control the drive module 500 based on one or more of the received signals from the sensors 22, 24, 26, 28, 30, 32, 34.

The auto injector 4 comprises an orientation sensor 22. The orientation sensor 22 is configured to provide an orientation signal indicative of the orientation of a cartridge received in the auto injector 4. For example, the orientation sensor 22 may be configured to detect the orientation of the auto injector 4. The orientation of the cartridge may be determined based on the orientation of the auto injector 4. The orientation sensor 22 may be configured to detect the direction of gravity. For example, the orientation sensor 22 may comprise an accelerometer.

The processing unit 20 is coupled to the orientation sensor 22. The processing unit 20 is configured to receive the orientation signal. The processing unit 20 may determine the orientation of the cartridge based on the orientation signal. The processing unit 20 may control the drive module 500 based on the orientation signal. For example, the processing unit 20 may be configured to control the drive module 500 to move the plunger rod to the first plunger rod position based on the orientation signal. For example, the processing unit 20 may be configured to control the drive module 500 to move the plunger rod to the first plunger rod position only if the cartridge outlet is pointing upwards, e.g. such that air is expelled from the cartridge compartment upon movement of the plunger rod to the first plunger rod position.

The auto injector 4 comprises a code sensor 24. The code sensor 24 is configured to read a cartridge code feature, and provide a code signal indicative of the cartridge code feature. For example, the code sensor may be configured to read/detect a colour code.

The processing unit 20 is coupled to the code sensor 24. The processing unit 20 is configured to receive the code signal. The processing unit 20 may determine the cartridge code feature of the cartridge assembly based on the code signal. The processing unit 20 may control the drive module 500 based on the code signal. For example, the processing unit 20 may be configured to control the drive module 500 to move the plunger rod to the first plunger rod position and/or the second plunger rod position based on the code signal. For example, the processing unit 20 may be configured to determine the position of the first plunger rod position based on the code signal.

The auto injector 4 comprises an ejection sensor 26, such as a plunger rod position sensor. The ejection sensor 26 is configured to detect the position of the plunger rod of the auto injector 4 and/or the position of the first stopper of the cartridge, and provide an ejection sensor signal indicative of the position of the plunger rod and/or first stopper.

The processing unit 20 is coupled to the ejection sensor 26. The processing unit 20 is configured to receive the ejection sensor signal. The processing unit 20 may determine the position of the plunger rod based on the ejection sensor signal. The processing unit 20 may control the drive module 500 based on the ejection sensor signal. For example, the processing unit 20 may be configured to control the drive module 500 to start, stop or continue movement of the plunger rod based on the ejection sensor signal. For example, the processing unit 20 may be configured to determine that the plunger rod is moved to the first plunger rod position based on the ejection sensor signal.

The auto injector 4 comprises a cartridge sensor 28. The cartridge sensor 28 is configured to detect reception of a cartridge assembly in the auto injector 4. The cartridge sensor 28 provides a cartridge sensor signal indicative of reception of a cartridge assembly.

The processing unit 20 is coupled to the cartridge sensor 28. The processing unit 20 is configured to receive the cartridge sensor signal. The processing unit 20 may control the drive module 500 based on the cartridge sensor signal. For example, the processing unit 20 may be configured to control the drive module 500 to start movement of the plunger rod if a cartridge assembly is received, and/or only if a cartridge assembly is received.

The code sensor 24 and the cartridge sensor 28 may be the same sensor, e.g. the code sensor 24 may be configured to detect reception of a cartridge assembly and subsequently read the cartridge code feature.

The auto injector 4 comprises a needle sensor 30. The needle sensor 30 is configured to detect a needle, and/or a needle assembly, and/or a needle cover of a needle assembly, of the cartridge assembly, when the cartridge assembly is received in the auto injector 4. The needle sensor 30 provides a needle signal indicative of the presence of a needle, and/or a needle assembly, and/or a needle cover of a needle assembly, of the cartridge assembly.

The processing unit 20 is coupled to the needle sensor 30. The processing unit 20 is configured to receive the needle signal. The processing unit 20 may control the drive module 500 based on the needle signal. For example, the processing unit 20 may be configured to control the drive module 500 to start movement of the plunger rod only if a needle is present, and/or only if a needle cover is not present.

The auto injector 4 comprises a temperature sensor 32. The temperature sensor 32 is configured to detect a temperature, such as a temperature of the auto injector and/or of the cartridge and/or of the medicament. The temperature sensor 32 is configured to provide a temperature signal indicative of the temperature.

The processing unit 20 is coupled to the temperature sensor 32. The processing unit 20 is configured to receive the temperature signal. The processing unit 20 may be configured to determine the temperature, such as the temperature of the auto injector and/or of the cartridge and/or of the medicament based on the temperature signal. The processing unit 20 may control the drive module 500 based on the temperature signal. For example, the processing unit 20 may be configured to control the drive module 500 to move the plunger rod to the first plunger rod position and/or the second plunger rod position based on the temperature signal. For example, the processing unit 20 may be configured to determine the position of the first plunger rod position based on the temperature signal.

The auto injector 4 comprises a resistance sensor 34. The resistance sensor 34 is configured to detect resistance against movement of the plunger rod of the auto injector 4. The resistance sensor 34 may be configured to detect resistance against movement of the plunger rod based on measurements of the drive module 500. For example, the resistance sensor 34 may be configured to detect the electrical current of a motor of the drive module 500. The resistance sensor 34 is configured to provide a resistance signal indicative of resistance against movement of the plunger rod.

The processing unit 20 is coupled to the resistance sensor 34. The processing unit 20 is configured to receive the resistance signal. The processing unit 20 may be configured to determine the resistance against movement of the plunger rod based on the resistance signal. The processing unit 20 may control the drive module 500 based on the resistance signal. For example, the processing unit 20 may be configured to control the drive module 500 to adjust movement of the plunger based on the resistance signal. For example, the processing unit 20 may be configured to control the drive module 500 to start, stop or continue movement of the plunger rod based on the resistance signal.

The auto injector 4 is illustrated comprising all of the above mentioned sensors. However, alternatively, the auto injector may comprise only one or any combination of one or more of the above mentioned sensors.

The auto injector comprises a trigger member 1102. The trigger member 1102 is configured to provide a trigger event upon activation. For example, the trigger member 1102 may be a contact member configured to be pressed against the injection site for activation.

The processing unit 20 is coupled to the trigger member 1102. The processing unit 20 is configured to receive the trigger event. The processing unit 20 may control the drive module 500 based on the trigger event. For example, the processing unit 20 may be configured to control the drive module 500 to move the plunger rod to the second plunger rod position following reception of the trigger event. The processing unit 20 may be configured to control the drive module 500 to move the plunger rod to the second plunger rod position, e.g. to inject the medicament, only after receiving the trigger event from the trigger member 1102.

The auto injector comprises a housing 6 accommodating the sensors 22, 24, 26, 28, 30, 32, 34, processing unit 20, trigger member 1102 and drive module 500.

Figure 8:
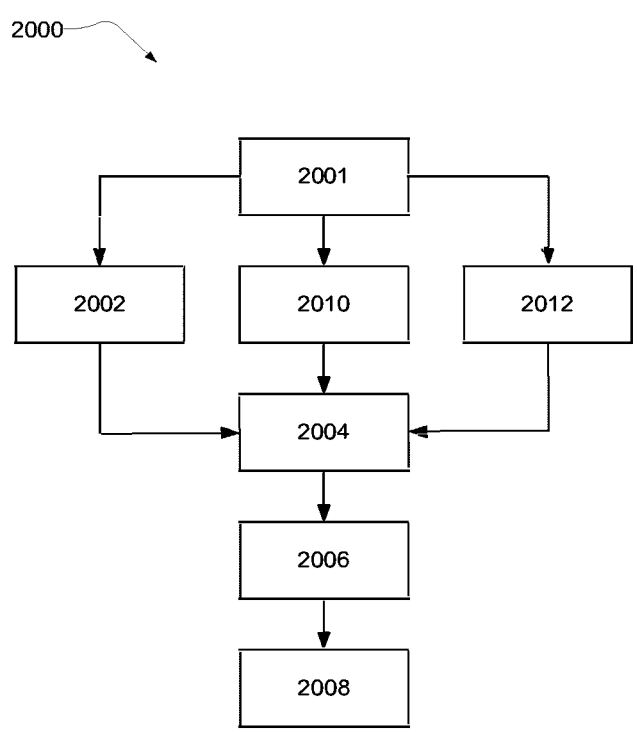
FIG. 8 shows a flow chart of an exemplary method.

FIG. 8 shows a flow chart of an exemplary method 2000 for operating an auto injector, such as the auto injector as described in relation to the previous figures. The method 2000 comprises receiving 2001 a cartridge assembly; reading 2002 a cartridge code feature of the cartridge assembly; moving 2004 a plunger rod of the auto injector to a first plunger rod position, wherein the first plunger rod position is based on the cartridge code feature; receiving a trigger event 2006; and moving 2008 the plunger rod to a second plunger rod position following reception of the trigger event.

The method 2000 furthermore comprises an optional step of determining 2010 an orientation of the cartridge. This step may be performed simultaneously with reading 2002 the cartridge code feature. However, alternatively the determining 2010 of the orientation may be performed before or after the reading 2002 of the cartridge code feature. If determining 2010 the orientation, movement 2004 of the plunger rod to the first plunger rod position may be based on the determined orientation. For example, the movement 2004 may require that the determined orientation is within a predefined range, e.g. of vertical.

The method 2000 furthermore comprises an optional step of detecting 2012 a temperature. This step may be performed simultaneously with reading 2002 the cartridge code feature and/or determining 2010 the orientation. However, alternatively the detecting 2012 of the temperature may be performed before or after the reading 2002 of the cartridge code feature and/or before or after the determining 2010 of the orientation. If detecting 2012 the temperature, the first plunger rod position may further be based on the detected temperature. Movement 2008 of the plunger rod to the second plunger rod position may be based on the detected temperature. For example, the speed of the movement 2008 may be based on the detected temperature.

Steps of the exemplary method 2000, especially the steps of reading 2002 a cartridge code feature of the cartridge assembly; optionally determining 2010 an orientation of the cartridge; optionally detecting 2012 a temperature; moving 2004 a plunger rod of the auto injector to a first plunger rod position; receiving a trigger event 2006; and moving 2008 the plunger rod to a second plunger rod position, may be controlled by a processing unit, such as the processing unit of the auto injector.

Exemplary auto injectors, cartridges, systems and methods are set out in the following items:

1. An auto injector for administering a medicament, comprising:
   a housing;
   a cartridge receiver configured to receive a cartridge assembly comprising a cartridge and a cartridge code feature, the cartridge containing the medicament;
   a code sensor configured to read the cartridge code feature;
   a drive module coupled to move a plunger rod; and
   a processing unit coupled to the code sensor and the drive module;
   the processing unit being configured to:
      receive from the code sensor a code signal indicative of the cartridge code feature; and
      control the drive module to move the plunger rod to a first plunger rod position, the first plunger rod position being based on the code signal.

2. Auto injector according to item 1, wherein the first plunger rod position is selected to expel air from the cartridge.

3. Auto injector according to any of items 1 or 2, wherein the processing unit is further configured to:
   receive a trigger event; and
   control the drive module to move the plunger rod to a second plunger rod position following reception of the trigger event.

4. Auto injector according to item 3 comprises a trigger member, and wherein the trigger event comprises activation of the trigger member.

5. Auto injector according any of items 3 or 4, wherein the trigger event is indicative of the auto injector being pressed against the injection site.

6. Auto injector according to any of the preceding items comprising an orientation sensor, wherein the processing unit is coupled to the orientation sensor, the processing unit being configured to receive from the orientation sensor an orientation signal indicative of the orientation of the cartridge when received in the cartridge receiver, and the processing unit being configured to control the drive module to move the plunger rod to the first plunger rod position based on the orientation signal.

7. Auto injector according to item 6, wherein the orientation sensor comprises an accelerometer.

8. Auto injector according to any of items 6 or 7, the processing unit being configured to control the drive module to move the plunger rod to the first plunger rod position if the orientation signal indicates that a tilt between vertical and a longitudinal axis extending along the cartridge is within 45 degrees of vertical and a cartridge outlet of the cartridge is in a vertical position above a cartridge compartment of the cartridge, the cartridge compartment containing the medicament.

9. Auto injector according to any of the preceding items, wherein the code sensor comprises an optical sensor.

10. Auto injector according to any of the preceding items, wherein the cartridge code feature comprises one or more of a colour, a bar code, an RFID tag, an NFC tag, an identification number, and a QR code.

11. Auto injector according to any of the preceding items comprising a temperature sensor configured to provide a temperature signal indicative of the temperature of the cartridge when received in the cartridge receiver, wherein the processing unit is coupled to the temperature sensor and configured to receive the temperature signal, and the processing unit being configured to control the drive module to move the plunger rod to the first plunger rod position based on the temperature signal.

12. Auto injector according to any of the preceding items, wherein the plunger rod is moved to the first plunger rod position with a first plunger rod speed based on the code signal.

13. A cartridge assembly for an auto injector comprising a cartridge and a cartridge code feature, the cartridge containing a medicament, the cartridge code feature being configured to be read by a code sensor of the auto injector for moving a plunger rod of the auto injector to a first plunger rod position based on the cartridge code feature.

14. Cartridge assembly according to item 13, wherein the cartridge comprises a cartridge compartment containing the medicament, a cartridge outlet, and a first stopper movable inside the cartridge compartment towards the cartridge outlet, wherein the cartridge code feature is indicative of a position of the first stopper wherein air in the cartridge compartment is reduced.

15. Cartridge assembly according to any of items 13 or 14, wherein the cartridge compartment has a first cartridge subcompartment containing a first medicament component of the medicament and a second cartridge subcompartment containing a second medicament component of the medicament, wherein the first medicament component is a fluid and the second medicament component is a lyophilized medicament.

16. A system comprising a cartridge assembly and an auto injector, the cartridge assembly comprising a cartridge and a cartridge code feature, the cartridge containing a medicament, the auto injector comprising:
  a housing;
  a cartridge receiver configured to receive the cartridge assembly;
  a code sensor configured to read the cartridge code feature;
  a drive module coupled to move a plunger rod; and
  a processing unit coupled to the code sensor and the drive module;
  the processing unit being configured to:
    receive from the code sensor a code signal indicative of the cartridge code feature; and
    control the drive module to move the plunger rod to a first plunger rod position, the first plunger rod position being based on the code signal.

17. System according to item 16, wherein the processing unit is further configured to:
  receive a trigger event; and
  control the drive module to move the plunger rod to a second plunger rod position following reception of the trigger event.

18. A method for operating an auto injector comprising a plunger rod, the method comprising:
  receiving a cartridge assembly comprising a cartridge and a cartridge code feature, the cartridge containing a medicament;
  reading the cartridge code feature; and
  moving the plunger rod to a first plunger rod position, the first plunger rod position being based on the cartridge code feature.

19. Method according to item 18 further comprising:
  receiving a trigger event;
  moving the plunger rod to a second plunger rod position following reception of the trigger event.

20. Method according to any of items 18 or 19, wherein the plunger rod is moved to the first plunger rod position with a first plunger rod speed based on the code signal.

The invention claimed is:
1. A system comprising an auto injector for administering a medicament and a cartridge assembly:
  wherein the cartridge assembly comprises a cartridge and a cartridge code feature, the cartridge comprising a cartridge compartment containing the medicament, and a cartridge outlet; and
  wherein the auto injector comprises:
    a housing;
    a cartridge receiver configured to receive the cartridge assembly;
    a code sensor configured to read the cartridge code feature;
    a drive module coupled to move a plunger rod;
    an ejection sensor configured to provide an ejection sensor signal indicative of a position of the plunger rod; and
    a processing unit coupled to the code sensor, the drive module and the ejection sensor, wherein the processing unit is configured to:
      receive from the code sensor a code signal indicative of the cartridge code feature;
      receive from the ejection sensor the ejection sensor signal indicative of the position of the plunger rod; and
      control the drive module to move the plunger rod to a first plunger rod position based on the ejection sensor signal, the first plunger rod position being based on the code signal;
      wherein air is expelled from the cartridge upon movement of the plunger rod to the first plunger rod position such that the air in the cartridge compartment is reduced to an amount appropriate for injection; and
      wherein the processing unit is configured to move the plunger rod to the first plunger rod position only when the cartridge outlet is pointing upwards.

2. The system according to claim 1, wherein the ejection sensor comprises a tachometer.

3. The system according to claim 1, wherein the processing unit is configured to determine that the plunger rod is positioned at the first plunger rod position based on the ejection sensor signal.

4. The system according to claim 3, wherein the ejection sensor signal includes a first ejection sensor signal indicative of a count of revolutions of the drive module and a second ejection sensor signal indicative of the plunger rod being in a known position.

5. The system according to claim 4, wherein the second ejection sensor signal is indicative of the plunger rod being in a fully retracted position.

6. The system according to claim 1, wherein the processing unit is further configured to:
  receive a trigger event; and
  control the drive module to move the plunger rod to a second plunger rod position following receipt of the trigger event.

7. The system according to claim 6, further comprising a trigger member, and wherein the trigger event comprises activation of the trigger member.

8. The system according to claim 6, wherein the trigger event is indicative of the auto injector being pressed against an injection site.

9. The system according to claim 1, further comprising an orientation sensor, wherein the processing unit is coupled to the orientation sensor, the processing unit being configured to receive from the orientation sensor an orientation signal indicative of the orientation of the cartridge when received in the cartridge receiver, and the processing unit being configured to control the drive module to move the plunger rod to the first plunger rod position based on the orientation signal.

10. The system according to claim 9, wherein the orientation sensor comprises an accelerometer.

11. The system according to claim 9, wherein the processing unit is configured to control the drive module to move the plunger rod to the first plunger rod position if the orientation signal indicates that a tilt between vertical and a longitudinal axis extending along the cartridge is within 45 degrees of vertical and a cartridge outlet of the cartridge is in a vertical position above the cartridge compartment.

12. The system according to claim 1, wherein the code sensor comprises an optical sensor.

13. The system according to claim 1, wherein the cartridge code feature comprises one or more of a colour, a bar code, an RFID tag, an NFC tag, an identification number, and a QR code.

14. The system according to claim 1, wherein the plunger rod is moved to the first plunger rod position with a first plunger rod speed based on the code signal.

15. A method for operating a system according to claim 1, the method comprising:
  receiving the cartridge assembly comprising the cartridge and the cartridge code feature, the cartridge containing the medicament;
  reading the cartridge code feature;
  receiving the ejector sensor signal; and
  moving the plunger rod to the first plunger rod position, the first plunger rod position being based on the cartridge code feature, and wherein when the plunger rod is positioned at the first plunger rod position, air is expelled from the cartridge, and
  wherein the plunger rod is only moved to the first plunger rod position if the cartridge outlet is pointing upwards.

* * * * *

UNITED STATES PATENT AND TRADEMARK OFFICE
CERTIFICATE OF CORRECTION

PATENT NO. : 11,969,581 B2
APPLICATION NO. : 17/816360
DATED : April 30, 2024
INVENTOR(S) : Per Mølgaard Pedersen et al.

It is certified that error appears in the above-identified patent and that said Letters Patent is hereby corrected as shown below:

On the Title Page

Page 3, Column 1 item (56) (Other Publications), Line 20, delete "08285," and insert -- 082856, --.

In the Specification

Column 13, Line 49, delete "400" and insert -- 400. --.

Column 18, Line 48, after "according" insert -- to --.

In the Claims

Column 22, Line 21, Claim 15, delete "the ejector sensor" and insert -- the ejection sensor --.

Signed and Sealed this
Twenty-third Day of July, 2024

Katherine Kelly Vidal
*Director of the United States Patent and Trademark Office*